United States Patent [19]

Schmitz

[11] Patent Number: 5,069,070
[45] Date of Patent: Dec. 3, 1991

[54] METHOD FOR DETERMINING THE ALCOHOL CONTENT AND/OR THE CALORIFIC VALUE OF FUELS VIA PROPAGATION PARAMETERS

[75] Inventor: Günter Schmitz, Aachen, Fed. Rep. of Germany

[73] Assignee: FEV Motorentechnik GmbH KG, Aachen, Fed. Rep. of Germany

[21] Appl. No.: 446,781

[22] Filed: Dec. 6, 1989

[30] Foreign Application Priority Data

Dec. 9, 1988 [DE] Fed. Rep. of Germany ....... 3841471

[51] Int. Cl.⁵ .............................................. G01H 5/00
[52] U.S. Cl. .................................... 73/597; 324/644; 324/645; 324/663; 324/667; 73/19.03
[58] Field of Search ...................... 73/597, 61.1, 19.03; 324/661, 663, 667, 644, 645

[56] References Cited

U.S. PATENT DOCUMENTS

| | | | |
|---|---|---|---|
| 3,688,188 | 8/1972 | Bak et al. ......................... | 324/58.5 |
| 3,965,416 | 6/1976 | Friedman ......................... | 324/58.5 |
| 4,429,273 | 1/1984 | Mazzagatti ....................... | 324/61 |
| 4,453,125 | 6/1984 | Kimura et al. ................... | 324/58.5 |
| 4,764,718 | 8/1988 | Revus et al. ..................... | 324/58.5 |
| 4,802,361 | 2/1989 | Bussian et al. .................. | 73/61.1 |
| 4,829,233 | 5/1989 | Flemming ......................... | 324/58.5 |
| 4,888,547 | 12/1989 | McGinn et al. .................. | 324/58.5 |
| 4,902,961 | 2/1990 | De et al. .......................... | 324/640 |
| 4,939,467 | 7/1990 | Nogami et al. .................. | 324/663 |
| 4,945,863 | 8/1990 | Schmitz et al. .................. | 123/1 A |

OTHER PUBLICATIONS

Proceedings of the Fourth International Symposium on Alcohol Fuels Technology, Sao Paulo, Brazil, Oct. 5, 1980, pp. 379–383.

Primary Examiner—Hezron E. Williams
Assistant Examiner—William Francos
Attorney, Agent, or Firm—Watson, Cole, Grindle and Watson

[57] ABSTRACT

Especially precise and reliable measurements and evaluations are obtained by measuring one or more propagation parameters of electromagnetic waves in a wave guide or resonator at least partially filled with fuel and evaluated in an evaluating circuit as the measure for the alcohol content and/or the calorific value. According to one embodiment, the travel time or the travel time difference of an electromagnetic wave between two or more points in a wave guide filled with fuel is determined and is evaluated through computer or circuit technology as the measure for the alcohol content and/or the calorific value.

6 Claims, 2 Drawing Sheets

METHOD FOR DETERMINING THE ALCOHOL CONTENT AND/OR THE CALORIFIC VALUE OF FUELS VIA PROPAGATION PARAMETERS

The present application relates to commonly owned U.S. patent applications Ser. No. 391,248, filed Aug. 9, 1987 and Ser. No. 329,839, filed March 23, 1989, which are hereby incorporated by reference.

BACKGROUND OF THE INVENTION

In light of diminishing fossil energy reserves of fuels obtained from crude oil and stricter environmental protection requirements, increasing amounts of methyl or ethyl alcohol are being added to these fuels. Thus, any arbitrary refueling should be possible both with pure fuels and mixed fuels. When the alcohol content is higher, it is necessary to know the blending ratio in order to obtain optimal performance from the fuel-burning engine and to enable a precise proportioning of fuel adjusted to the operating conditions. The continuous determination of the alcohol content in the fuel fed into the fuel-burning engine in operation presents special problems for automobile engines in which any possible blend may be present by arbitrary refueling with various types of fuel.

The known optical processes are hardly suitable for this purpose since they often utilize interface effects to determine the refraction index, from which the alcohol content can be inferred. In addition to the difficulty of using these processes in automobile engines, another drawback of this process is that the mix to be observed must have a high homogeneity, especially at the interface. The required precision has not been achieved with this process.

Therefore, it has been proposed that the alcohol content in fuels be determined by means of a dielectric analysis. Such a process would solve the problem concerning measurement of the interface effects since measurement is done volumetrically. On the other hand, the conductance of the mixture significantly affects the volumetric dielectric analysis, i.e., cross sensitivity. Since the conductance is a function primarily of the pollutants or the water content, such a measuring process leads to useless results.

The possibility of determining the alcohol content of fuels by means of dielectric measurements is explored in the document "Proceedings of the Fourth International Symposium on Alcohol Fuels Technology," Sao Paulo, Brazil of Oct. 5, 1980. However, the process was rejected since the influences of temperature and conductance induced by water content or other pollutants in the fuel prevented a reliable measurement suitable for fuel-burning engines from being obtained.

Therefore, it is an object of the present invention to provide a process of the aforementioned kind which permits a precise and reliable determination of the alcohol content and/or calorific value in fuels, in particular for application in automobile engines.

Other objects and advantages are apparent from the specification and drawings which follow.

SUMMARY OF THE INVENTION

The foregoing and additional objects are obtained by a process for the determination of the alcohol content and/or the calorific value of fuels wherein one or more propagation parameters of electromagnetic waves are measured in a wave guide or resonator filled at least partially with fuel and are evaluated in an evaluating circuit as the measure for the alcohol content and/or the calorific value.

According to a preferred embodiment a wave guide filled with fuel is provided and the travel time or the travel time difference of an electromagnetic wave between two or more points is determined and evaluated by means of a computer or circuitry as the measure for the alcohol content and/or the calorific value.

It can also be expedient to evaluate the travel time of a reflected wave as the measure for the alcohol content and/or the calorific value.

To obtain a higher accuracy of measurement and/or to compensate at least in part for the influence of pollutants or additives of the fuel, it is expedient to determine several of the propagation parameters and to evaluate combinations of them.

To attain advantages in light of noise immunity with respect to temperature influences and electromagnetic irradiation, size, contacting, electric wiring, noise radiation and the like, the measuring circuit and, if desired, also the evaluating circuit can be completely or partially integrated into the wave guide or resonator.

DETAILED DESCRIPTION OF THE PREFERRED EMBODIMENTS

Figure 1:
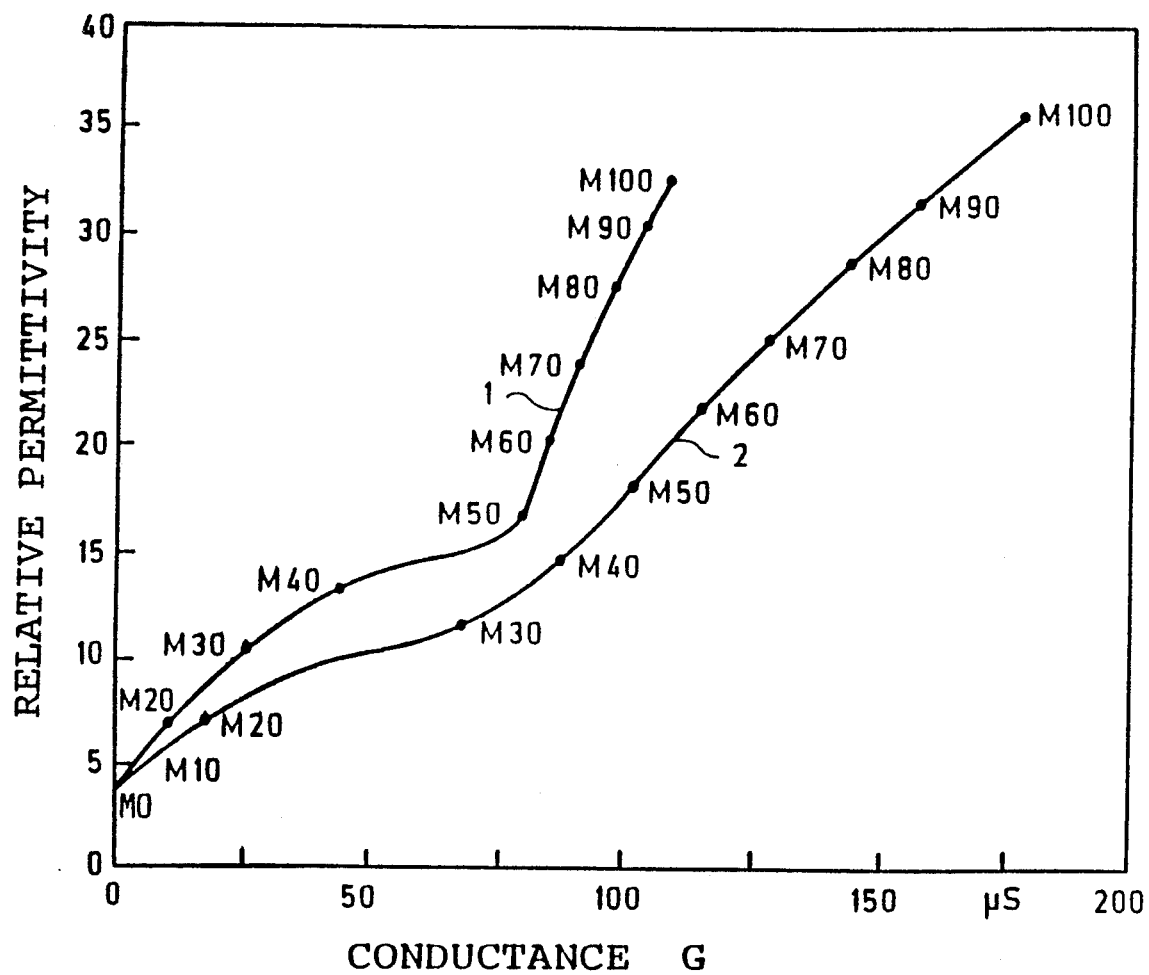
FIG. 1 is a diagram of the relative permittivity as a function of the conductance G as a function of the water content and the methanol content of the fuel.

The present invention will now be described in greater detail with reference to the accompanying drawings. Referring to FIG. 1, the values of the relative permittivity are plotted on the ordinate and the conductance is plotted on the abscissa. Curve 1 shows the values of the relative permittivity as a function of the proportion of methanol admixture with 0% water content in the fuel, whereas line 2 plots the corresponding values with 2.5% $H_2O$ content. The measured points for the variable percentages of methanol, ranging from 0% to 100% (M0 to M100), are plotted on the curves.

It is clear that with higher percentages of water, specific dielectric values are measured at higher conductivities. With a combined measurement of the conductance and relative permittivity, empirically determined families of plotted curves of the kind shown in FIG. 1 enable a correction of the dielectric measurement by determining the conductance.

By knowing the conductance, the cross influences on the capacitance due to the pollutants of the fuel can now be corrected. As FIG. 1 shows, a higher percentage of water in the fuel, for example, increases the capacitance. By measuring the conductance, this increase in the capacitance can be taken into consideration when the alcohol content is being determined.

During the evaluation, the conductivity related to the length is marked G′, whereas the capacitance, related to the length, which in turn depends on the dielectric constants, is marked C'. Thus, the result for the wave impedance, for example, is:

$$Z_L = (R' + jwL')^{\frac{1}{2}} * (G' + jwC')^{-\frac{1}{2}}$$

wherein R' stands for the resistance per unit length formed by the line, L' stands for a measure for the inductance per unit length, and $w = 2\pi f$ and f stands for the operating frequency.

The attenuation factor $\alpha$ and the image phase constant $\beta$ are computed according to the formula:

$$\alpha + j\beta = ((R' + jwL') * (G' + jwC'))^{\frac{1}{2}}$$

The propagation velocity or phase velocity V is computed as:

$$V = (L'C')^{-\frac{1}{2}}$$

According to a preferred embodiment, the propagation velocity or phase velocity of an electromagnetic wave, which depends to a fair degree on the dielectric constant of the medium with which the wave guide is filled, is determined as the propagation parameter. Thus, the mixing ratio or the calorific value can be determined by means of a computer or a circuit from the propagation velocity.

Other advantages can be achieved if the propagation velocity is determined by measuring the travel time or the travel time difference between two or more points. In this process, the propagation velocity does not have to be determined as such but rather the travel time or the travel time difference can serve directly to determine the alcohol content or the calorific value by means of a computer or a circuit.

Figure 2:
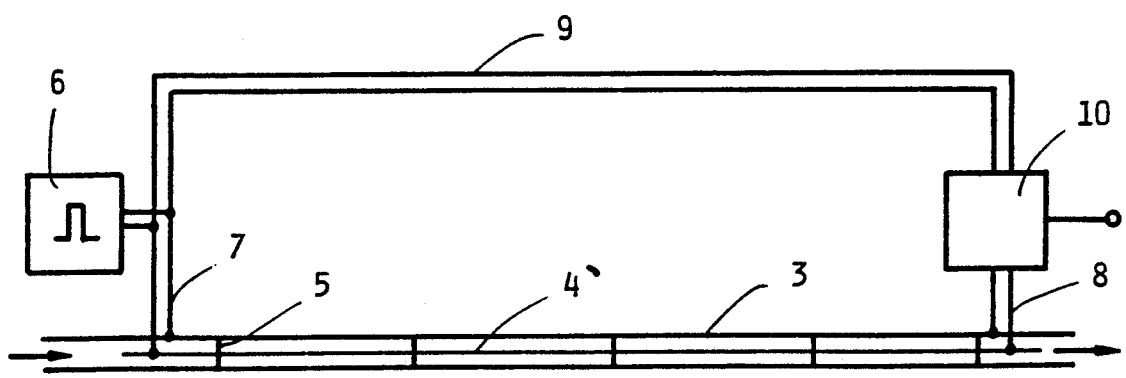
FIG. 2 is a schematic view showing a circuit to determine the propagation velocity by measuring the travel time or the travel time difference between two points.

A preferred embodiment of such a circuit is schematically shown in FIG. 2. Fuel flows through a fuel line 3 of, e.g., an internal combustion engine having a sheath in which an inner conductor 4 is installed and serving as a wave guide. Conductor 4 is held in the center of line 3 by centering discs 5.

A pulse generator 6 generates a square wave pulse, which is coupled at an input 7 into the wave guide formed by the fuel line 3. At an output 8 the pulse is tapped again and compared to the original pulse, fed over line 9, in an evaluating circuit 10. The travel time difference represents a measure for the wave propagation velocity and varies according to the composition. The alcohol content or the calorific value can then be evaluated from this in a subsequent evaluating computer.

Many variations will be readily apparent to one skilled in the art. For example, a reflection of the pulse can also be caused by means of a wave impedance change in the wave guide, e.g., of the inner conductor 4. Following the double travel time needed for a distance, the reflected pulse arrives again at the input 7. This travel time can then be determined directly at the input 7 so that the additional line 9 can be eliminated.

In a modified embodiment, the installation of the inner conductor 4 can also be eliminated if one works with adequately high frequencies, which lie on the far side of the so-called cut-off frequency of the wave guide, formed in this case by the fuel line 3.

Other advantages follow from determining the cut-off frequency of the wave guide formed by the fuel line 3. The cut-off frequency is that frequency above which wave propagation is possible. In addition to geometrical properties of the line, this cut-off frequency depends on the compositional values of the substances and in particular on the relative permittivity. Thus, the cut-off frequency also represents a measure for the alcohol content.

The cut-off frequency can in turn be determined in a number of ways. FIG. 2 shows two preferred embodiments. A tunable frequency generator 31 supplies a wave guide 32 filled with fuel at the supply point 33. A detector 35, which determines whether a signal can still be detected at this point, is connected to the tapping point 34. The frequency above which a signal can no longer be detected, i.e, the cut-off frequency, then represents the measure for the alcohol content or the calorific value. A second embodiment uses a detector 36, which is fastened to the supply point 33 and which can determine by measuring the voltage or the current at the supply point 33 where the supplied frequency is transported by the wave guide. Each frequency above the cut-off frequency is not transported but rather reflected at the supply point 33, which yields other current and voltage ratios at the supply point 33. These ratios are determined by the detector 36. The frequency, starting from the frequency which the voltage ratios change, e.g., when the voltage increases, represents a measure for the alcohol content or the calorific value.

If both ends of a wave guide are not terminated with the characteristic impedance of the wave guide, a resonator is provided whose resonance frequency depends, among other things, directly on the phase velocity of the wave in the wave guide. Thus, it can be quite advantageous to design a part of the fuel system as a resonator in which the measurement of the resonance frequency can be used to determine the relative permittivity of the medium, i.e., the fuel, in the wave guide.

There are special advantages in using already available parts of the fuel system such as the fuel compartment as the resonator. This component of the fuel system is usually made of a conductive material and has a rectangular cross-section which can be used directly as the so-called wave guide or also as cavity resonator.

Figure 4:
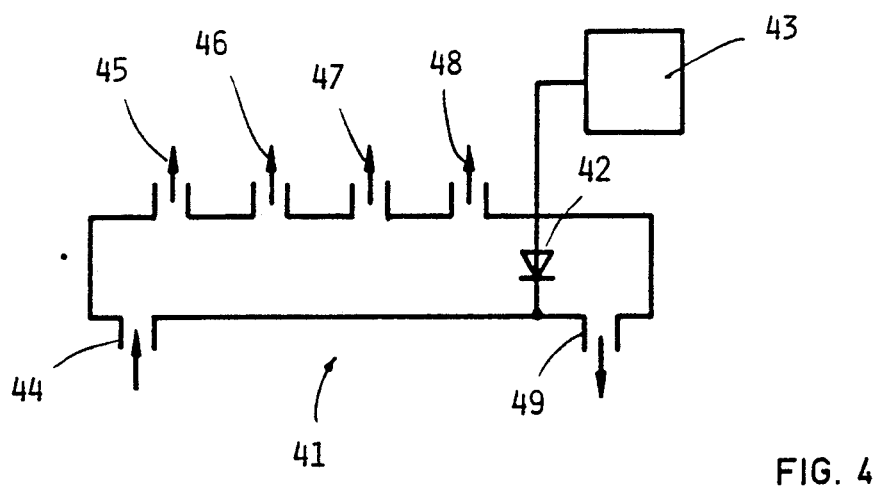
FIG. 4 shows an embodiment applying the process of the invention to a fuel system of a fuel-burning engine.
Figure 3:
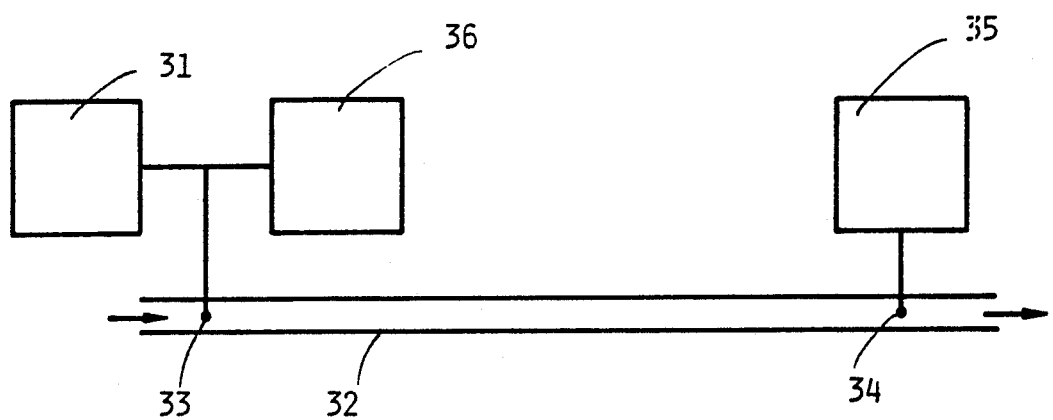
FIG. 3 is a schematic view of a device for determining the alcoholic content and/or calorific values of fuels according to the present invention.

FIG. 4 shows an embodiment of the present invention which uses a resonator. An active high frequency component 42, e.g., a Gunn element, an avalanche effect diode or a tunnel diode, is used to determine a resonance frequency. A specific resonance frequency, which depends on the filling medium and through whose measurement in a circuit 43 the alcohol content or the calorific value can be determined, is impressed on this component by means of the resonator 41. In this embodiment the resonator is fed by fuel through supply line 44. The injection nozzles are supplied as shown by arrows 45, 46, 47 and 48 and a part of the fuel leaves the resonator 41 through discharge line 49 again in the direction of the pressure control valve.

To evaluate this relatively high resonance frequency, the resonance frequency can be reduced by mixing with a second frequency in a frequency range that is more accessible to evaluation. For instance, the resonance frequency may be mixed with a lower frequency and the resulting frequency may be used to calculate the alcohol content or the calorific value.

Special advantages are achieved with respect to size, noise sensitivity, noise irradiation, and temperature influence when all of the measuring and evaluating electronics or a part thereof are integrated into the system containing the fuel as in the cavity resonator described above.

Among other things, the characteristic impedance of a wave guide is also determined by means of the value of the substances contained in the wave guide. Thus, the relative permittivity of the material also has a strong influence on the characteristic impedance. The determination of this variable and from it in turn the finding of the alcohol content or the calorific value are possible by measuring the characteristic impedance of a wave guide filled with fuel.

The characteristic impedance may be determined by comparing the different amplitude or phase of the signal reflected at a transition point to a known wave impedance. The characteristic impedance of the wave guide may also be determined by measuring the amplitude or phase of the current and/or of the voltage.

A combination of the measured propagation parameters such as the imaginary and real part of the characteristic impedance and/or the travel times and/or the resonance frequencies can increase the accuracy of the determination of the alcohol content or the calorific value, since in this manner one can compensate, for example, for the negative influence of the pollutants on the measurement.

The dispersive behavior of the wave guide may be determined by providing a line at the input which is fed with a pulse of a specific shape, e.g., a square. Due to the dispersive behavior of the line filled with fuel, different frequency portions with different propagation velocities are guided on the line. The result is a pulse distortion. The pulse shape is analyzed at the end of the line and, from this, conclusions about the dispersion of the medium contained in the wave guide and thus about the mixing ratio or the calorific value of the fuel are drawn via a computer or a measuring circuit.

In addition, the temperature of the fuel can be determined and used to compensate for the temperature influence to obtain a more accurate determination of the alcohol content and/or the calorific value.

When the process of the invention is applied to the control and adjustment of injection fuel-burning engines, it is expedient to proceed in such a manner that the measurement of the alcohol content and/or the calorific value of the supplied fuel serves to pre-control the injected quantity, whereas the air ratio is precision controlled by means of a known lambda control. In this manner, other advantages are gained if the measuring and/or evaluating circuit is integrated into the injection system using circuit or programming technology.

Propagation parameters include phase velocity, image phase constant, attenuation factor, characteristic impedance, dispersion and line wave length. All of these variables depend on the parameters of the fuels with which the high frequency line or the resonator is filled.

In particular, these variables depend on the dielectric constants, which in turn depend on the blending ratio that is used. Furthermore, the conductivity enters into this propagation parameter, which also depends on the blending ratio yet is also influenced by the additives or the pollutants in the fuel.

In particular, the advantages of the process of the invention lies in the relative independence of the propagation parameters from geometric variables so that manufacturing tolerances hardly play a role. The result is a more cost-efficient production since balancing operations to compensate for the manufacturing tolerances can be waived and even larger tolerances are acceptable.

Other modifications and improvements will be apparent to one skilled in the art without departing from the spirit and scope of the present invention as defined in the following claims.

I claim:

1. A method for determining an alcohol content and calorific value of a fuel, comprising the steps of:
   providing a hollow electrically terminated waveguide for the fuel;
   producing an electromagnetic wave having a defined frequency in the waveguide filled with the fuel;
   measuring a phase velocity of the electromagnetic wave where the phase velocity is defined as the product of the frequency and twice the distance between two voltage maxima of a standing wave in the waveguide; and
   comparing the measured phase velocity with a reference standard phase velocity previously measured in said hollow waveguide; and
   calculating the alcohol content and calorific value from the velocity ratio.

2. The method according to claim 1, wherein the provided wave guide is a fuel line of an internal combustion engine.

3. A method for determining an alcohol content and calorific value of a fuel, comprising the steps of:
   providing a hollow waveguide for the fuel;
   producing an electromagnetic wave in the waveguide filled with the fuel;
   measuring a cut-off frequency, below which the propagation of the electromagnetic wave ceases;
   comparing this cut-off frequency to a reference standard cut-off frequency previously measured in said hollow waveguide; and
   calculating the alcohol content and calorific value from the frequency ratio.

4. The method according to claim 3, wherein the provided waveguide is a fuel line of an internal combustion engine.

5. A method for determining an alcohol content and calorific value of a fuel, comprising the steps of:
   providing a hollow waveguide for the fuel;
   producing an electromagnetic pulse in the waveguide filled with the fuel;
   measuring the dispersion of the pulse in the fuel, where dispersion is defined as the difference of the phase velocities of the lower portion of the frequency spectrum of the pulse and the phase velocities of the higher portion of the frequency spectrum of the pulse and measuring those differences of the phase velocities,
   comparing said differences to a known reference standard difference of phase velocities previously measured in said hollow waveguide; and calculating the alcohol content and calorific value from the velocity difference ratio.

6. The method according to claim 5 wherein the provided waveguide is a fuel line of an internal combustion engine.

* * * * *